United States Patent [19]

Struve

[11] 4,148,810

[45] Apr. 10, 1979

[54] PROCESS FOR ISOLATING STEROLS FROM FAT PROCESSING RESIDUES

[75] Inventor: Alfred Struve, Hilden, Fed. Rep. of Germany

[73] Assignee: Henkel Kommanditgesellschaft auf Aktien, Dusseldorf-Holthausen, Fed. Rep. of Germany

[21] Appl. No.: 857,898

[22] Filed: Dec. 6, 1977

[30] Foreign Application Priority Data

Dec. 11, 1976 [DE] Fed. Rep. of Germany ....... 2656208

[51] Int. Cl.² .............................................. C07J 9/00
[52] U.S. Cl. .............................................. 260/397.25
[58] Field of Search ................................... 260/397.25

[56] References Cited

U.S. PATENT DOCUMENTS 2,568,202  9/1951  Overhof et al. ................. 260/397.25

*Primary Examiner*—Elbert L. Roberts
*Attorney, Agent, or Firm*—Hammond & Littell

[57] ABSTRACT

A method for isolating sterols from the distillation residues of industrial fat processing comprising transesterifying said residues with methanol and then isolating said sterols from the transesterification mixture by adduct formation with $CaCl_2$ in an aprotic solvent and with slight addition of a protic solvent.

6 Claims, No Drawings

PROCESS FOR ISOLATING STEROLS FROM FAT PROCESSING RESIDUES

FIELD OF THE INVENTION

The invention relates to a method of isolating sterols from the distillation residues of industrial fat processing, especially those residues from the recovery of fatty acids or fatty esters from fats. These residues are enriched with the sterols as substances of low volatility, which are partly in the form of fatty acid esters.

RELATED ART

All hitherto known processes for recovering sterols are relatively expensive. Such processes are almost always preceded by a saponification step in order to liberate the sterols from their fatty esters. These processes are described in German Pat. Nos. 838,642, 875,515, U.S. Pat. Nos. 2,573,891, 2,610,195, German Auslegeschrift No. 1,077,824 and Hungarian Pat. No. 156,413. After the saponification, the sterol is isolated by solvent extraction together with the other unsaponifiable constituents. It can be separated from the unsaponifiables by crystallization or by adduct formation with metal salts, dicarboxylic acids, HCl, urea, etc., especially with $CaCl_2$, $ZnCl_2$ and oxalic acid. The crystallization procedure is described in German Pat Nos. 833,815 and 859,620 and the adduct formation procedure is described in German Pat. Nos. 827,199, 882,090, 929,424, Recueil 69 (1950) 433, Dutch Offenlegungschrift No. 6,706,583, U.S. Pat. No. 2,598,468 and German Offenlegungschrift No. 1,768,394.

The sterol can also be crystallized out from methanol together with a portion of the soap, after saponification of the fatty acid distillation residue. By dissolving out the sterol with a solvent, e.g. 1,2-dichloroethane, and precipitating it from this solvent with a little methanol/$H_2O$, a pure sterol is obtained in relatively good yield from a process based on soy fatty acid distillation residues. This process is described in U.S. Pat. Nos. 2,729,656 and 3,840,570. This process is however not readily applicable to the majority of the other residues from repeated fat splitting, especially those from waste tallow.

Finally, the sterol can also be crystallized out directly after complete esterification (yielding the methyl ester) of the distillation residues. In this case, the liberation of the sterol results from transesterification. Frequently, there is also a saponification step followed by a further esterification. This method can, however, be applied satisfactorily only to sterol-enriched autoclave condensates. This process is described in U.S. Pat. Nos. 2,704,764 and 3,335,154.

OBJECTS OF THE INVENTION

An object of the present invention is the development of a method for isolating sterols by relatively simple means and in good yield with good purity from the distillation residues of fat processing, especially from those difficult to handle residues of the processing involving repeated splitting to fatty acids or methyl esters of fatty acids.

Another object of the present invention is the development of a method for isolating sterols from the distillation residues of industrial fat processing, which comprises transesterification of the distillation residues with methanol and a subsequent isolation of the sterols from the transesterification mixture by adduct formation with $CaCl_2$ in an aprotic solvent which contains a small amount of a protic solvent.

These and other objects of the present invention will become more apparent as the description thereof proceeds.

DESCRIPTION OF THE INVENTION

The present invention concerns an improved method for isolating sterols from the distillation residues of industrial fat processing, especially from those residues obtained from the recovery of fatty acids or esters of fatty acids from fats. These residues are enriched with the sterols, which are present as substances of low volatility, and partly as fatty acid esters. According to the process of the invention sterols of high purity are recovered by relatively simple means and in good yield from the difficult to handle residues obtained from the repeated splitting of fats to fatty acids or to the methyl esters of such fatty acids.

The invention relates to a method for isolating the sterols from the distillation residues of industrial fat processing, which comprises transesterification of the distillation residues with methanol and a subsequent isolation of the sterols from the transesterification mixture by adduct formation with $CaCl_2$ in an aprotic solvent which contains a small amount of a protic solvent.

More particularly, the invention relates to a method for isolating the sterols from distillation residues of fat processing, comprising (a) heating the distillation residues in a sufficient amount of methanol at elevated temperatures, preferably at temperatures of 180°–240° C., to produce a transesterified residue containing sterols, (b) separating the transesterified residue containing sterols from the methanol, (c) dissolving the transesterified residue in an aprotic solvent to form a solution thereof, (d) adding calcium chloride and a small amount of a protic solvent to the solution in amounts sufficient to form an adduct of calcium chloride with sterol, (e) heating the solution at a temperature, preferably 20°–100° C., and for a time sufficient to form an adduct of calcium chloride with sterol, (f) separating the adduct and then decomposing it to the free sterol, and (g) recovering the sterol.

The residues, remaining from the distillation of fatty acids and fatty acid methyl esters after the initial splitting or transesterification of the fats, and preferably after an at least once repeated splitting or transesterification by which the sterol content is raised further, are black substances, which are partly liquid, partly solid at room temperature, yet melt below 50° C. In the case of residues from fatty acid distillations, the acid numbers lie at about 20–80, the saponification numbers at about 120–160 and the iodine numbers at about 50–110. For transesterification residues from a methyl ester distillation, the acid numbers are less than 10, the saponification numbers about 140–180 and the iodine numbers about 50–110. In spite of the previous treatment of the fats by transesterification, sterol liberation by a further transesterification is required, because reesterification of the sterol occurs as a rule during the methyl ester distillation as a result of the high temperatures employed. The sterol content of the two types of residues mentioned amounts to about 5–15% in the case of double and triple splitting of fats.

The transesterification to liberate sterol from the distillation residues is carried out in methanol, a weight ratio of methanol to residue of 1:1 being preferred. The conversion temperature is advantageously 180°-240° C., preferably 200°-220° C. By means of this transesterification with methanol at elevated temperatures, free fatty acids present are esterified. The sterol esters are transformed into free sterols plus methyl esters of fatty acids. A basic catalyst such as an alkali metal alcoholate, for example, sodium methylate or an alkali metal hydroxide, for example, KOH, can be added in amounts of about 0.1-1%, as e.g. 0.5%, by weight, based on the amount of residue. However, the transesterification also takes place without catalyst, though in some cases at a clearly slower rate. The transesterification is carried out for the time needed to liberate the sterols. It takes about three hours at 220° C. or about six hours at 180° C. After the conversion, the catalyst, if present, is neutralized with dilute acid, e.g. dilute $H_2SO_4$, and the solution is then evaporated at temperatures up to 120° C. The residue is washed with water and dried at temperatures up to 120° C. If washing proves to be difficult, the methanolic phase may also be separated out after the conversion by the addition of relatively small amounts of water, further washing being then dispensed with.

For adduct formation, the transesterified residue is taken up in an aprotic solvent. Ligroin, 1,2-dichloroethane, toluene, dialkyl ketones, as e.g. containing 3-6 carbon atoms, such as acetone and, methyl ethyl ketone, ethyl acetate, etc. are very suitable as aprotic solvents. The amount of solvent added can be varied from about ½ to several times the amount of residue by weight, ½ to 2-times the amount, however, being preferred. Insoluble constituents may be removed from the resulting solutions by filtration or centrifugation, optionally after treating the solution with animal charcoal or filter aids.

Calcium chloride is used as the adduct former. The powdered technical product, whose $CaCl_2$ content is about 95-98%, is preferably used. The weight of $CaCl_2$ to be added for adduct formation corresponds approximately to the weight of sterol contained in the residue. It can however be varied upward or downwards, depending on the requirements of the particular residue. Preferably, the weight ratio of sterol to $CaCl_2$ is about 1:0.5 to 1:2.

Adduct formation takes place with the addition of a small amount of a protic solvent, preferably methanol or water. The amount of protic solvent, such as methanol or water, corresponds approximately to the amount of calcium chloride. In any particular case, it must however be determined depending on the residue being treated. As a rule, the weight ratio of $CaCl_2$ to methanol is from 3:1 to 1:2. In the case of water addition, smaller amounts can be used, the weight ratio of $CaCl_2$ to $H_2O$ falling between 4:1 and 3:2. A combination of $CaCl_2$:$H_2O$ even down to a weight ratio of 1:1 has been found useful.

The special advantage of the process of the invention lies in the addition of a protic solvent, preferably water or methanol, for adduct formation. Without this addition, the quality and yield of adduct are insufficient. For example, when technical $CaCl_2$ powder is used by itself, almost no adduct is obtained within a reasonable conversion period from the transesterified residue in ligroin. Poor yields are obtained by this process in ethyl acetate. These process deficiencies are overcome by the addition of protic solvents, so that well crystallized adducts are obtained in high purity from aprotic solvents even when $CaCl_2$ of technical quality is used.

The adduct formation takes place while the solution is stirred intensively at temperatures from ca. 20° to 100° C. The time required depends on the amount of protic solvent used. As a rule, it amounts to about one hour at about 40°-60° C. After adduct formation, crystallization is then allowed to proceed for about 1-2 hours while cooling carefully to 20°-25° C. The adduct and unconverted $CaCl_2$ are separated by filtering or centrifuging. The adduct, after being washed with solvent and dried under vacuum at about 50° to 100° C., is then decomposed to the free sterol in water and a solvent or with water by itself. For this purpose, the adduct is stirred for 15 minutes to one hour at 20° to 50° C. The solvent phase contains the sterol and is washed with water, filtered and evaporated. As a rule, an about 75-95% pure sterol is obtained in yields of about 50-80%.

The sterols, whether of vegetable or animal origin, are valuable raw materials for the pharmaceutical and cosmetic industry. They may be converted into valuable steroid intermediates by fermentative degradation. Cholesterol finds individual application in the manufacture of vitamin $D_3$ and in the field of liquid crystals in the optical industry.

The following examples are illustrative of the practice of the invention without being limitative in any manner.

EXAMPLES

EXAMPLE 1

(a) Transesterification

A residue of 100 gm was obtained from a fatty acid recovery process after a triple splitting and distillation. The residue had the following characteristic values: acid number 54, saponification number 153, hydroxyl number 13, and iodine number 75. The residue was a mixture derived from animal and vegetable fats and had a sterol content of 9.3% of the following composition: 55% cholesterol, 32.6% sitosterol, 7.6% campesterol, and 4.8% stigmasterol. To this residue were added 1000 gm of methanol and 16.7 gm of a 30% methanolic sodium methylate solution. The batch was heated with stirring for three hours in an autoclave at 220° C. The product from autoclaving was neutralized with 45.3 gm of 10% aqueous sulfuric acid. Methanol and water were then distilled off. Towards the end of the distillation, a water aspirator vacuum was applied and the temperature was raised to 120° C. The distillation residue was then washed twice with 300 gm quantities of water at ca. 50° C. and finally dried under vacuum at temperatures up to 120° C. A black substance, liquid at room temperature, was obtained in a yield of 970 gm; its acid number was 9.3, saponification number 136, hydroxyl number 68 and iodine number 70.

(b) Adduct Formation 250 gm of the transesterification product from procedure 1a above were taken up in 125 gm of ligroin (b.p. 80°-110° C.) and stirred for ten minutes with 5 gm of filter aid. The filter aid was filtered off. 8 gm of methanol were added as protic solvent to the filtrate, followed by 24 gm of powdered, technical calcium chloride (purity 95-98%). The mixture was heated for one hour with stirring to ca. 40° to 60° C. It was then allowed to cool to 22° to 25° C. during one and a half hours. The crystallizate was filtered off on a Buchner funnel and washed immediately with ligroin. The filter cake was dried under vacuum at 50° C. 42 gm of a gray/white solid substance were obtained, which consisted of a mixture of $CaCl_2$-sterol adduct and $CaCl_2$-methanol and melted above 160° C. This substance was mixed with 500 gm of ethyl acetate and 500 gm of water and decomposed while stirring for 15 minutes at 50° C. into $CaCl_2$ and sterol. The ethyl acetate phase was washed with water, filtered warm and evaporated. After drying at 50° C. under vacuum, 18.9 gm of a sterol mixture were obtained with a sterol content of 93.4%. The yield, based on the sterol content of 9.3% in the residue, was 76.4%.

EXAMPLE 2

25 gm quantities of the transesterification product from Example 1a were treated with different solvents and additives in accordance with the procedure set forth in Example 1b. In place of the 125 gm of ligroin used in Example 1b, the amounts of the solvents presented in the following Table I were used. Similarly, the amounts of the additives listed in the following Table I were used in place of the 8 gm of methanol and 24 gm of calcium chloride used in Example 1b. The results are shown in the following Table I:

Table 1

| Solvent | Additives | Yield % Sterol | Purity % Sterol |
| --- | --- | --- | --- |
| a) 12.5 g Ligroin | 0.8 g $H_2O$<br>2.4 g $CaCl_2$ | 74.7 | 86.8 |
| b) 12.5 g Toluene | 0.8 g $H_2O$<br>2.4 g $CaCl_2$ | 73.7 | 95.1 |
| c) 12.5 g Diethyl Ketone | 0.8 g Methanol<br>2.4 g $CaCl_2$ | 65.1 | 84.3 |
| d) 12.5 g Ethyl acetate | 0.8 g Methanol<br>2.4 g $CaCl_2$ | 63.4 | 86.7 |
| e) 12.5 g 1.2-dichloroethane | 0.8 g Methanol<br>2.4 g $CaCl_2$ | 62.9 | 93.7 |

EXAMPLE 3

(a) Transesterification 1000 gm of a residue from the recovery of fatty acid methyl esters from tallow were used. The residue, obtained after double transesterification and distillation, had the following characteristic values: acid number 4, saponification number 159, hydroxyl number 40.5, iodine number 61.5, and a sterol content of 9% (free sterol: less than 4%). The sterol composition was 98.5% cholesterol and 1.5% vegetable sterols. 1000 gm of methanol and 16.7 gm of a 30% methanolic sodium methylate solution were added to this residue. The remainder of the transesterification procedure was carried out as in Example 1a. 960 gm of a black substance, liquid at room temperature, with an acid number of 9.3, a saponification number of 158, a hydroxyl number of 45.9 and an iodine number of 61, were obtained.

(b) Adduct Formation 250 gm of the transesterification product from procedure 3a above were mixed with 125 gm of ligroin, (b.p. 80°-110° C.). 24 gm of methanol and 24 gm of powdered, technical calcium chloride were added to the mixture. The rest of the procedure was carried out as in Example 1b. 28.5 gm of a gray/white solid substance were obtained. Decomposition in ethyl acetate/water yielded 15 gm of a yellow/white sterol of 97.7% purity. The yield, based on the 9% sterol content in the residue, was 65.1%.

EXAMPLE 4

Several batches, each containing 25 gm of the transesterification residue from Example 3a and 12.5 gm of ligroin (b.p. 80°-110° C.), were treated in accordance with the procedure set forth in Example 3b with the amounts of the protic solvents and $CaCl_2$ listed in the following Table II. The % yield and % purity of the sterol obtained for each batch are given in Table II.

Table II

| | Additive | | | |
| --- | --- | --- | --- | --- |
| | Methanol g | $H_2O$ g | $CaCl_2$ g | Yield % Sterol | Purity % Sterol |
| a) | 1.6 | | 2.4 | 56.4 | 79.4 |
| b) | 0.8 | | 2.4 | 83.7 | 75.5 |
| c) | 1.6 | | 1.6 | 53.8 | 94.5 |
| d) | | 1.6 | 1.6 | 50.9 | 76.4 |
| e) | | 0.8 | 2.4 | 68.5 | 75.2 |

EXAMPLE 5

(a) Transesterification 1000 gm of a residue from the recovery of fatty acids from tallow were used. The residue was obtained after a triple splitting and distillation and had these characteristic values: acid number 19, saponification number 124, hydroxyl number 13, iodine number 75 and a cholesterol content of 14%. The transesterification was carried out essentially as described in Examples 1a and 3a. After the neutralization, however, a methanolic phase separated out on addition of ca. 100 gm of water. The heavier fatty phase was dried. 962 gm of a black substance, solid at room temperature and having an acid number of 4, a saponification number of 110, a hydroxyl number of 69 and an iodine number of 64, were obtained.

(b) Adduct Formation 170 gm of the transesterification product from procedure 5a above were taken up in 170 gm of ligroin (b.p 100°-140° C.). The undissolved portion (ca. 3%) was centrifuged off. 24 gm of methanol and 20 gm of calcium chloride powder were added. The subsequent procedure was carried out as in Example 1b. 36 gm of a gray/white solid substance were obtained. Decomposition with water yielded 17 gm of cholesterol with a m.p. of 138° to 140° C. and a purity of 94%. The yield, based on a 14% sterol content in the residue, was 68%.

The preceding specific embodiments are illustrative of the practice of the invention. It is to be understood, however, that other expedients known to those skilled in the art, or disclosed herein, may be employed without departing from the spirit of the invention or the scope of the appended claims.

I claim:

1. A method for isolating sterols from the distillation residue of fat processing, comprising
   (a) transesterifying a distillation residue with a sufficient amount of methanol at temperatures of 180°-240° C. to liberate the sterols,
   (b) separating the transesterified residue containing sterol from the methanol,
   (c) dissolving the transesterified residue in an aprotic solvent selected from the group consisting of ligroin, toluene, diethylketone, ethyl acetate and 1,2-dichloroethane to form a solution thereof, (d) adding calcium chloride and a small amount of a protic solvent selected from the group consisting of methanol and water to the solution in amounts sufficient to form an adduct of calcium chloride with sterol, (e) separating the adduct and then decomposing it to the free sterol, and (f) recovering the sterol, wherein in step (d) the weight ratio of sterol to calcium chloride for adduct formation is 1:0.5 to 1:2, the weight ratio of calcium chloride to methanol is from 3:1 to 1:2 and the weight ratio of calcium chloride to water is from 4:1 to 3:2.

2. The method according to claim 1, wherein the transesterification with methanol is carried out at temperatures of 200°–220° C.

3. The method according to claim 1, wherein the aprotic solvent is a member selected from the group consisting of ligroin and toluene.

4. The method according to claim 1, wherein the transesterification with methanol is carried out in the presence of a catalyst selected from the group consisting of alkali metal alcoholate and alkali metal hydroxide.

5. The method according to claim 1, wherein powdered technical calcium chloride is used for adduct formation with sterol.

6. The method according to claim 1, wherein the distillation residue is obtained from the recovery of fatty acids or methyl esters of fatty acids from fats.

* * * * *